(12) United States Patent
Capdevila et al.

(10) Patent No.: US 10,695,488 B2
(45) Date of Patent: Jun. 30, 2020

(54) DEVICE FOR LIMITING THE INJECTION PRESSURE OF A MEDICAL INSTRUMENT FOR INTRODUCING A FLUID

(71) Applicant: Pajunk GmbH Medizintechnologie, Geisingen (DE)

(72) Inventors: Xavier Capdevila, Montferrier sur Lez (FR); Olivier Choquet, Castelnau le Lez (FR); Siddharth Desai, Ladera Ranch, CA (US)

(73) Assignee: Pajunk GmbH Medizintechnologie, Geisingen (DE)

( * ) Notice: Subject to any disclaimer, the term of this patent is extended or adjusted under 35 U.S.C. 154(b) by 267 days.

(21) Appl. No.: 15/771,929

(22) PCT Filed: Jun. 10, 2016

(86) PCT No.: PCT/EP2016/063389
§ 371 (c)(1),
(2) Date: Apr. 27, 2018

(87) PCT Pub. No.: WO2017/071833
PCT Pub. Date: May 4, 2017

(65) Prior Publication Data
US 2018/0318504 A1 Nov. 8, 2018

Related U.S. Application Data

(60) Provisional application No. 62/285,447, filed on Oct. 30, 2015.

(51) Int. Cl.
*A61M 5/168* (2006.01)
*A61M 5/31* (2006.01)
(Continued)

(52) U.S. Cl.
CPC .... *A61M 5/16813* (2013.01); *A61M 5/16881* (2013.01); *A61M 5/31* (2013.01);
(Continued)

(58) Field of Classification Search
CPC ........ A61M 5/2033; A61M 5/20; A61M 5/30; A61M 39/26; A61M 39/24; A61M 5/2053
See application file for complete search history.

(56) References Cited

U.S. PATENT DOCUMENTS

| 4,403,988 A | 9/1983 | Binard et al. |
| 2003/0225371 A1 | 12/2003 | Hadzic et al. |

(Continued)

FOREIGN PATENT DOCUMENTS

WO 2003101526 A1 11/2003

OTHER PUBLICATIONS

Patent Cooperation Treaty, "International Search Report" and translation thereof, issued in International Application No. PCT/EP2016/063389, by European Searching Authority, document of 4 pages, dated Jul. 13, 2016.

*Primary Examiner* — Manuel A Mendez
(74) *Attorney, Agent, or Firm* — Akerman LLP; Peter A. Chiabotti (57) ABSTRACT

A device for limitation of the injection pressure of a medical instrument for introduction of a fluid, having a housing, with an entrance of the housing for introducing the fluid at an inlet pressure, with an outlet of the housing for introducing the fluid to the instrument, with a flow-through channel of the housing connecting the entrance and the outlet and with a plunger guided in the housing which is impinged on by the pressure of the fluid and through this pressure is movable against a resetting force. On the plunger a blocking element is arranged, which is located in the flow cross section of the flow-through channel, and that the blocking element releases (Continued)

the flow cross section, when the pressure of the fluid impinging on the plunger lies beneath a value preset by the resetting force, and blocks the flow cross section when the pressure of the fluid impinging on the plunger exceeds this preset value and moves the plunger against the resetting force.

20 Claims, 11 Drawing Sheets

(51) Int. Cl.
*A61M 39/24* (2006.01)
*A61M 5/158* (2006.01)

(52) U.S. Cl.
CPC ............ *A61M 39/24* (2013.01); *A61M 5/158* (2013.01); *A61M 2005/3125* (2013.01); *A61M 2005/3128* (2013.01); *A61M 2039/242* (2013.01); *A61M 2039/2473* (2013.01); *A61M 2205/0272* (2013.01)

(56) References Cited

U.S. PATENT DOCUMENTS

| | | |
|---|---|---|
| 2006/0149214 A1 | 7/2006 | Breiter et al. |
| 2010/0179488 A1 | 7/2010 | Spiegel et al. |

10 PSI

FIG.10

15 PSI

FIG.12

25 PSI

FIG.14

SECTION K-K

FIG.11

SECTION L-L

FIG. 16  DETAIL G

DEVICE FOR LIMITING THE INJECTION PRESSURE OF A MEDICAL INSTRUMENT FOR INTRODUCING A FLUID

CROSS REFERENCE TO RELATED APPLICATIONS

This application is a § 371 National Phase of PCT/EP2016/063389, filed Jun. 10, 2016, which claims priority to U.S. Provisional Patent Application No. 62/285,447, filed Oct. 30, 2015.

BACKGROUND

The application relates to a device for limiting the injection pressure of a medical instrument for introducing a fluid according to the features and structures disclosed herein.

SUMMARY

What is designated in medicine as injection is parenteral introduction of a fluid, as a rule a liquid. The fluid is administered relatively quickly, for which it is introduced into the body at a certain pressure. The pressure can be generated manually, such as by a syringe plunger, or also by means of a pump. The injection pressure at which the fluid is introduced, in most cases may not exceed a certain critical pressure, since otherwise damage may be inflicted. The instrument for introducing the fluid is a cannula in most cases. However, the disclosure is also applicable for other medical instruments that serve for introducing a fluid, such as syringes, catheters, etc. In what follows the disclosure is described in connection with a cannula. Use in connection with other medical instruments is done in an obviously corresponding manner.

With peripheral nerve blocking in anesthesia, a fluid, i.e. an anesthetic, is injected into the nerve to be blocked. For this it is important to apply the anesthetic as close as possible to the nerve, to achieve effective anesthesia. On the other hand, the anesthetic may not be injected into the nerve, because under certain circumstances this could cause severe damage to the nerve. The position of the cannula during injection as a rule is set through electrical stimulation and/or by ultrasonic detection. Additionally, the position of the cannula syringe can be checked by observing the pressure that develops due to differing tissue resistance upon injection into the cannula. Perineural tissue offers relatively low resistance, while the resistance rises considerably if the cannula syringe meets the epineurium surrounding the nerve and especially the nerve fascicle. A user who carries out the injection can feel this injection pressure, since it resists the user's effort to move the syringe stamp forward. However, for the user to feel injection pressure is unreliable. Therefore, it was attempted to objectively determine injection pressure of the cannula, to more reliably avoid injection of the anesthetic into the nerve.

For this purpose, it is known from U.S. Pat. No. 4,403,988 to insert a device between the syringe and the cannula, which has a flow-through channel that connects the syringe with the cannula. Laterally from this flow-through channel an outlet channel branches off, which is closed by a spring-loaded plunger. If during injection, the cannula syringe meets a higher tissue resistance, because the cannula syringe hits the nerve or penetrates into it, then a higher injection pressure builds up in the cannula and thus in the flow-through channel of the device. If this injection pressure exceeds the value preset by the spring loading of the plunger, then the plunger is moved against the resetting force of the spring out of its closed setting and releases the outlet channel. The anesthetic can come out of the outlet channel, as long as the injection pressure is above this preset value, so that the injection pressure is reduced. Since the injection pressure is limited through this device to the preset value, a user who carries out the injection cannot determine any increase in injection pressure above the preset value, so that under certain circumstances he does not notice the wrong position of the cannula syringe, and the result can be nerve damage.

From WO 03/101526 A1 a device is known that is inserted between the syringe and the cannula and has a flow-through channel connecting the syringe with the cannula. The flow-through channel connects with a pressure chamber which is limited by a membrane. If the injection pressure rises in the flow-through channel, and thus in the pressure chamber, then the membrane is deflected out and presses an indicator pin against the force of a spring, so that this indicator pin is moved out to differing distances from the housing of the device to correspond to the injection pressure prevailing in the flow-through channel, through which, via colored ring coding of the indicator pin, the injection pressure can be visually monitored. The device merely shows the injection pressure, but does not automatically limit same. Avoidance of a damaging injection therefore depends on how promptly the user conducting the injection notices the display and takes the measures resulting from this.

The present disclosure provides a device for limitation of injection pressure which reliably prevents an incorrect injection, independent of the person carrying out the injection.

The present disclosure provides a device with the features and structures disclosed herein.

Advantageous embodiments are disclosed herein.

The disclosed device has a flow-through channel, through which the fluid to be injected, especially for example an anesthetic, flows from a syringe activated by the person carrying out the injection to a cannula to be inserted in the body of the patient. The injection pressure prevailing in the cannula, and thus in the flow-through channel, impinges on a plunger supported in the housing of the device, and can move same against a resetting force, if the injection pressure exceeds a value preset by the resetting force. On the plunger a blocking element is arranged by which the plunger moves. The blocking element is movable in the flow cross section of the flow-through channel. If the injection pressure is below the preset value, then the blocking element releases the flow cross section, so that the fluid to be injected can flow from the syringe through the flow-through channel to the cannula. If the injection pressure exceeds the preset value, so that the plunger is moved against the reset force, then the blocking element is moved by means of the plunger into a blocked setting in which the blocking element blocks the flow cross section. As soon as the injection pressure exceeds the preset value, the device thus automatically blocks the flow of anesthetic through from the syringe to the cannula, so that the syringe pressure no long acts on the anesthetic in the cannula and no anesthetic is injected. By this means, independent of the user, and with no temporal delay, the anesthetic is reliably prevented from being unintentionally injected into the nerve tissue with the higher tissue resistance.

The preset value of injection pressure at which the device locks, depends on various factors, especially for example the dimensions of the cannula, i.e. the length and interior diameter of the cannula, and on the patient, for example the age of the patient. In one advantageous embodiment of the disclosure, the reset force acting on the plunger with the blocking element is adjustable, so that the preset value of injection pressure can be adjusted according to the case of application. This especially advantageous if the device is a separate component that is inserted between the syringe and the cannula. Thus, a unitary component can be used for various cases of application, wherein the permissible injection pressure can be chosen and set corresponding to the cannula and appropriate for the patient.

In another embodiment, the disclosed device can be integrated in the proximal base of the cannula. Since in this case the cannula dimensions are set, adjustability of the permissible injection pressure can here be dispensed with, so that the design of the device is simpler, and usage of the device requires no additional measures.

In one advantageous embodiment, the adjustability of the resetting force acting on the plunger, and thus the adjustment of the permissible injection pressure is implemented in such a way that the resetting force engages on one side on the plunger and on the other side on a bracing piece of the housing, wherein this bracing piece is axially adjustable in the housing, to adjust the resetting force.

The resetting force especially is a spring force, which preferably is caused by a helical compression spring. The helical compression spring is arranged coaxially to the plunger stroke path and on the one side is braced on the plunger and on the other side on the support piece of the housing. In another embodiment, the resetting force can be a magnetic force. For this, preferably the magnetic repelling force of two permanent magnets is used, of which one is arranged on the plunger and the other on the support piece of the housing. Other possibilities for generating the resetting force are available to one skilled in the art. These possibilities include, for example, elastically compressible elements made of rubber or foam, as well as compressible closed air or gas volumes.

Appropriately the entrance and exit of the flow-through channel, and thus of the device, lie in a longitudinal axis line, so that the entrance-side-connected syringe and the exit-side-connected cannula are aligned to be axially aligned. In one advantageous embodiment, the plunger is arranged coaxial to the flow-through channel and the longitudinal axis line, wherein the blocking element is designed as a valve disk able to be moved axially by the plunger. This embodiment has the advantage of a slimmer outer contour of the device.

In another embodiment, the plunger is able to move perpendicular to the longitudinal axial line and the flow-through channel. The blocking element is able to move perpendicular to the longitudinal midline in the flow-through channel, and in the blocking setting it closes the syringe-side entrance of the flow-through channel.

The device preferably is made as a cost-effective plastic part, which can also be used as a disposable article.

BRIEF DESCRIPTION OF THE DRAWINGS

In what follows, the features and structures of the present disclosure are explained in greater detail using the embodiment examples shown in the figures. Shown are.

DETAILED DESCRIPTION

The first embodiment shown in FIGS. 1 to 14 has a housing 10, which essentially has the shape of a hollow circular cylinder. At the proximal end of housing 12, an entrance 12 is configured, which has the form of an attachment, with which a storage container not shown can connect, from which a fluid can be introduced under pressure into housing 10. Such a storage device preferably is configured as a syringe, by which an anesthetic is administered. The attachment of entrance 12 is configured for example as a female Luer-Lok attachment.

Into the distal end of housing 10, an interior tube 14 is inserted. Interior tube 14 runs coaxially in housing 10, with the outer diameter of interior tube 14 being smaller than the inner diameter of housing 10, so that a cylindrical space is formed between interior tube 14 and housing 10. Interior tube 14 on its end that points upstream in housing 10 is open and forms a circular-ring-shaped valve seat 16. The distal, downstream end of interior tube 16 projects out of housing 10 and forms an outlet 18, which is configured as an attachment, with which a cannula not shown can be connected for the injection. Outlet 18 is configured for example as a male Luer-Lok attachment.

The proximal end area of housing 10 forms a stroke space 20 in which a plunger 22 can be moved axially. Plunger 22 is guided so as to be axially movable on interior tube 14. On its outer circumference, plunger 22 is sealed by sealing lips 24 against the inner wall of housing 10. On its inner circumference, plunger 22 is sealed by an inner sealing lip 26 against the outer circumference of interior tube 14.

On the front side of plunger 22 facing entrance 12, a hollow cylindrical stub 28 is shaped, which is closed by a valve disk 30. Valve disk 30 has the shape of a circular disk, the diameter of which projects over the outer diameter of interior tube 14. The wall of stub 28 is interrupted by flow-through openings 32. On the front end of valve disk 30, directed upstream toward entrance 12, spacer tabs 34 are shaped, distributed over the circumference and opposite each other in the circumferential angle.

For generation of a resetting force acting on plunger 22, interior tube 14 is surrounded coaxially by a helical compression spring 36. Helical compression spring 36 is braced with its end facing upstream on plunger 22. The other end, facing downstream, of helical compression spring 36, is braced on a support piece 38, which is configured as an inside collar, which is directed inward into the housing against interior tube 14.

In an alternative embodiment, helical compression spring 36 can also be inserted coaxially into interior tube 14. Helical compression spring 36 is braced with its upstream-directed end on valve disk 30 of plunger 22. The downstream-directed end of helical compression spring 36 is braced on support piece 38, which in this embodiment is configured as an inside collar in interior tube 14.

Figure 1:
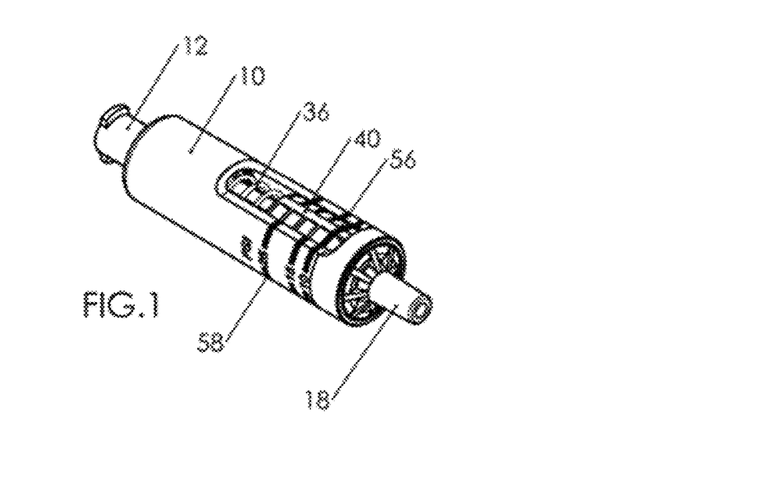
FIG. 1 a perspective view of a device of the disclosure in a first embodiment FIG. 2 an axial section through this device FIG. 3 an exploded view of the device FIG. 4 an axial section of the device in the flow-through setting in the setting with low injection pressure FIG. 5 an axial section as per FIG. 4 of the device in the blocked setting FIG. 6 an axial section as per FIG. 4 of the device in the flow-through setting in the setting with a high injection pressure FIG. 7 an axial section as per FIG. 6 of the device in the blocked setting FIG. 8 a perspective view of the device as per FIG. 1 in the setting with high injection pressure FIG. 9 in a perspective view, the inner tube of the device in the first embodiment FIG. 10 in a side view, the inner tube and the adjustment sleeve in the setting with low injection pressure FIG. 11 a section through the line K-K in FIG. 10
Figure 2:
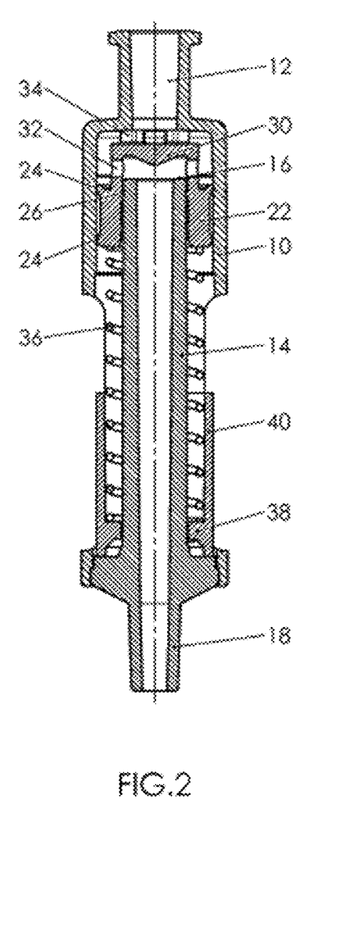
Figure 3:
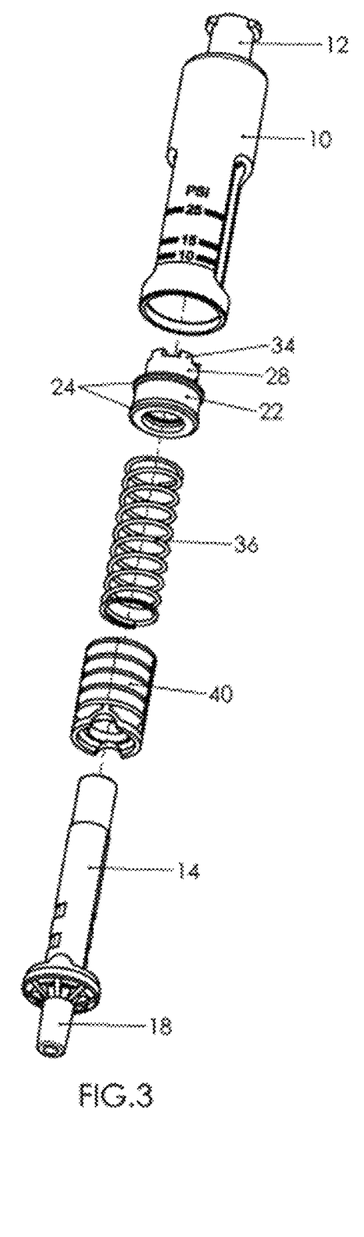
Figure 4:
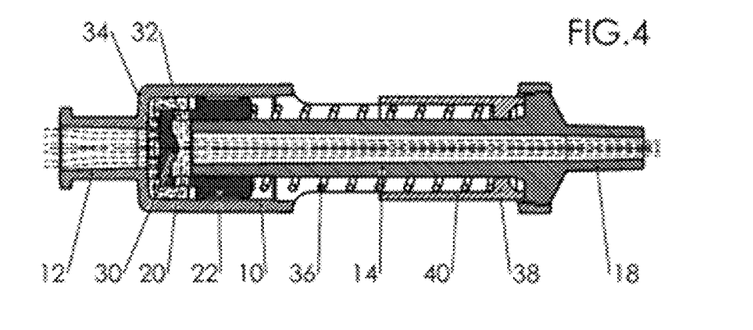
Figure 5:
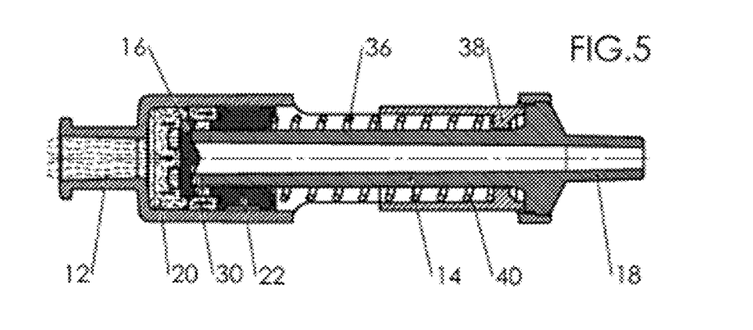

FIGS. 4 and 5 explain the function of the device. For injection of a fluid, for example a peripheral nerve block, a syringe is connected with the attachment forming entrance 12, and the cannula for the injection is connected with the attachment forming outlet 18.

Initially the spring force of helical compression spring 36 presses plunger 22 against the inflow direction, i.e. toward the left in FIGS. 4 and 5. The leftward motion of plunger 22 is limited in that spacer tabs 34 make contact with the entrance-side front wall of housing 10. Thereby valve disk 30 does not close entrance 12. The through-flow openings 32 are located axially before valve seat 16 of interior tube 14. If a user carrying out the injection operates the syringe, the anesthetic is introduced through entrance 12, passes between spacer tabs 34, flows around valve disk 30, passes through through-flow openings 32 and gets into interior tube 14, through which it is directed to outlet 18 and thus into the cannula. The flow path of the anesthetic is shown by dashed lines in FIGS. 4 and 5. In this flow-through setting shown in FIG. 4, the fluid can thus flow through the device unimpeded and be injected via the cannula.

If the cannula tip encounters greater tissue resistance, for example upon encountering the epineurium or by penetrating into the nerve, then flow through the cannula becomes more difficult and the pressure exerted by the user on the syringe results in an increasing stagnation pressure, which builds up in the cannula, in interior tube 14 and in the inner space of housing 10 upstream of plunger 22. When this stagnation pressure, which corresponds to the injection pressure acting on the cannula tip, exceeds a preset value which is set by the spring force of helical compression spring 36, then this stagnation pressure compresses plunger 22 against the spring force of helical compression spring 36 to the right in the setting shown in FIG. 5, in which the force generated by the pressure is shown by arrows. If plunger 22 on interior tube 14 is pushed to the right into the blocked setting shown in FIG. 5, then valve disk 30 seats on the valve seat 16 formed by the free inner end of interior tube 14 and blocks interior tube 14. The flow-through openings 32 are slid axially via interior tube 14, so that also these flow-through openings 32 are closed. Thereby the passage of the anesthetic through the device is totally blocked, and no more force is exerted on the anesthetic in the cannula.

Even if the user does not notice the risky impingement of the cannula and continues to exert pressure on the syringe stamp, a harmful injection is reliably precluded. If the user becomes aware of resistance when operating the syringe and withdraws the cannula from the incorrect position, helical compression spring 36 can again move the plunger into the flow-through setting shown in FIG. 4, so that, following the correction of the cannula position, the injection can be continued.

The injection pressure at which the device automatically locks, is preset by the spring force of helical compression spring 36. The injection pressure depends on various factors. For example, these are the particular patient's tissue condition, the inner diameter and length of the cannula, and the injection rate. Therefore, it is advantageous for the user if he can adjust the injection pressure at which the device automatically locks for these factors.

This is made possible in advantageous fashion in that the initial tension of helical compression spring 36 and thus the resetting force generated by this helical compression spring 36 is adjustable.

Figure 6:
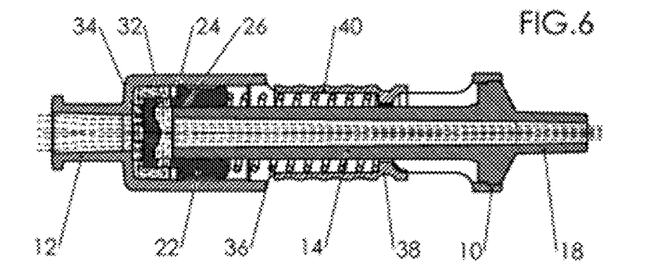
Figure 7:
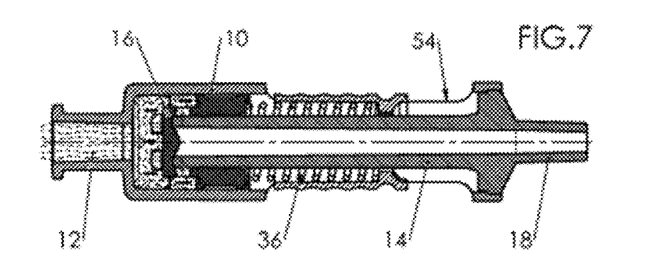
Figure 8:
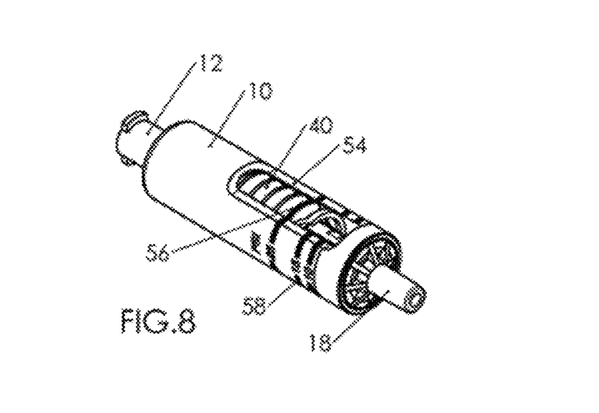
Figure 9:
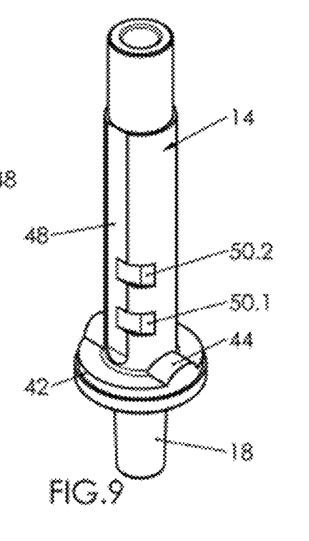

For this, preferably support part 38, on which helical compression spring 36 is braced, is adjustable in the axial direction of helical compression spring 36, so that helical compression spring 36 can be adjustably pretensioned. For this, support part 38 for this is configured as an inside collar of an adjustment sleeve 40. Adjustment sleeve 40 coaxially surrounds interior tube 14 and helical compression spring 36 seated on interior tube 14. Adjustment sleeve 40 is movable coaxially in housing 10 and can be fixed in the desired axial position. FIGS. 6, 7 and 8 show in the depictions as per FIGS. 1, 4 and 5 the device with a setting of adjustment sleeve 40 that pretensions helical compression spring 36, through which through-flow is blocked only at a higher injection pressure.

The way spring force is set is perceived in particular in FIGS. 9 to 14. Here as examples, three setting values for permissible injection pressure are depicted, namely 10 psi, 15 psi and 25 psi (0.7 bar, 1.0 bar and 1.7 bar). With a setting at the lowest injection pressure of 10 psi that triggers the blocking function (FIGS. 10 and 11), adjustment sleeve 40 sits axially on a flange 42, with which interior tube 14 is attached in housing 10. A nose 44 of flange 42 engages into a recess 46 of adjustment sleeve 40 and holds same in torque-free fashion on interior tube 14. Interior tube 14 on its outer jacket surface has two plane-parallel flat surfaces 48, which have a diametrical interval A, which is smaller than the outer diameter of interior tube 14. Further, interior tube 14 has two pairs of notches 50.1 and 50.2 at different axial distances from flange 42. The pair of notches 50.1 has plane-parallel surfaces which are arranged at a diametric interval A and arranged to be offset by 45° relative to flat surfaces 48. The pair of notches 50.2 in design and position matches notches 50.1, but these are axially displaced vis-à-vis notches 50.1. Adjustment sleeve 40 has a circular inner diameter that matches the circular outer diameter of interior tube 14. The circular inner diameter in an area of the end of adjustment sleeve 40 facing flange 42 is made narrower by two secant surfaces 52 that are arranged to be plane-parallel, diametrical to each other, which have an interval A in the clear.

Figure 10:
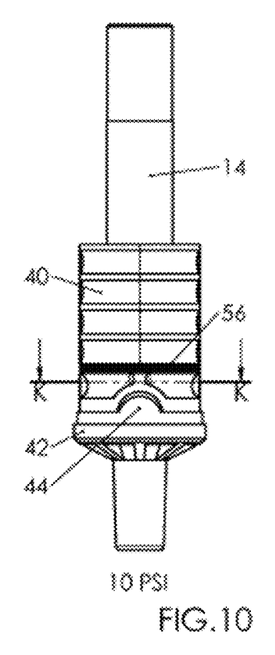
Figure 11:
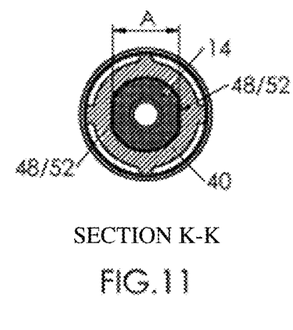

As is evident from FIGS. 10 to 14, adjustment sleeve 40, and thus helical compression spring 36, is adjusted in the following way. In the setting with the least pretensioning of the spring, which is shown in FIGS. 10 and 11, adjustment sleeve 40 is in such a rotational setting on interior tube 14 that the secant surfaces 52 projecting inward align with flattened surfaces 48 of interior tube 40. Adjustment sleeve 40 therefore can move downward on interior tube 14 (in the depiction of FIGS. 10 to 14), i.e., against flange 42 until adjustment sleeve 40 sits on flange 42 and nose 44 engages into recess 48, as shown in FIGS. 10 and 11. At this lowest spring pretensioning and thus least spring force acting on plunger 22, the device locks at an injection pressure of 10 psi, for example.

Figure 12:
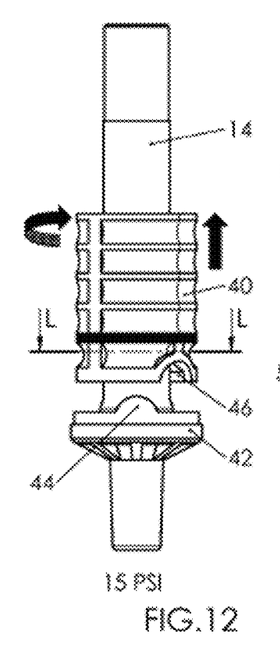
FIG. 12 a depiction as per FIG. 10 in the setting with a medium injection pressure FIG. 13 a section along line L-L in FIG. 12
Figure 13:
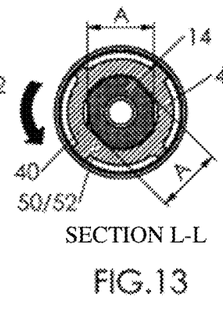
Figure 14:
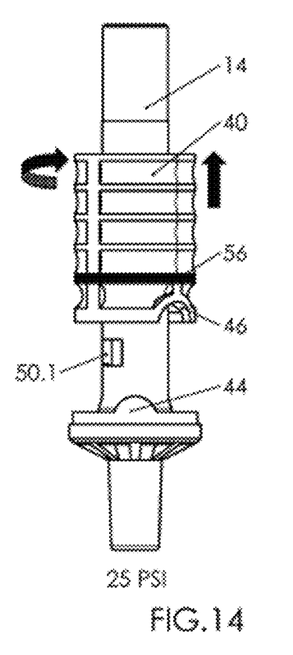
FIG. 14 a view as per FIG. 10 in the setting with high injection pressure FIG. 15 an axial section of the disclosed device in a second embodiment FIG. 16 an enlarged partial section from FIG. 15
Figure 15:
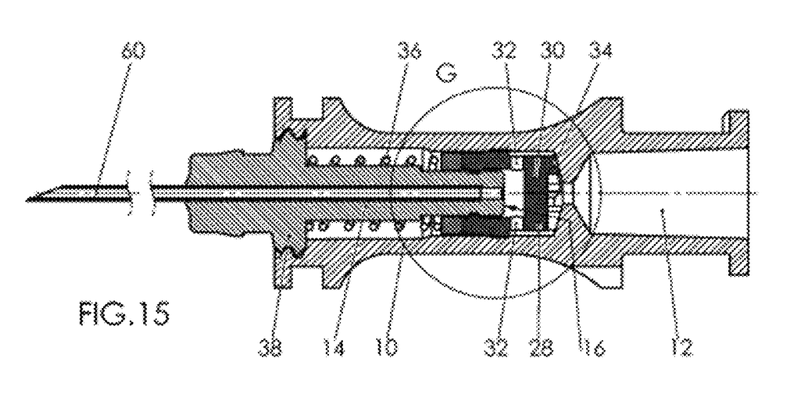
Figure 16:
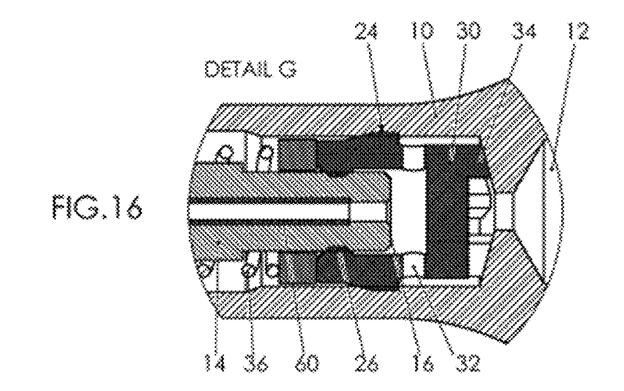
Figure 17:
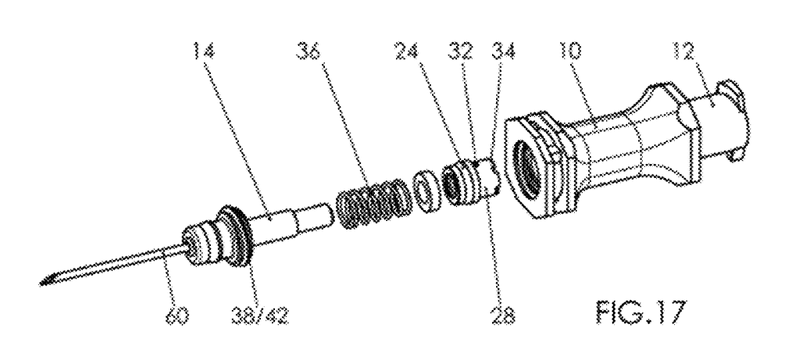
FIG. 17 an exploded view of the device in the second embodiment
Figure 18:
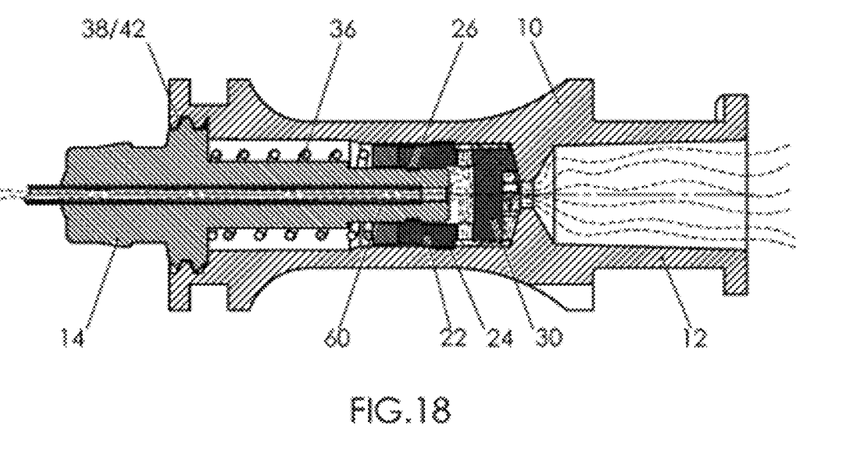
FIG. 18 an axial section of the device in the second embodiment in the flow-through setting FIG. 19 an axial section as per FIG. 18 in the blocked setting FIG. 20 a perspective view of the disclosed device in a third embodiment FIG. 21 an axial section through the device of FIG. 20 in the flow-through setting FIG. 22 a partial axial section as per FIG. 21 in the blocked setting FIG. 23 in a perspective view, a device according to the disclosure in a fourth embodiment FIG. 24 an axial section through this device FIG. 25 an axial section of the device in the flow-through setting in the setting with low injection pressure FIG. 26 an axial section as per FIG. 25 of the device in the blocked setting FIG. 27 an axial setting as per FIG. 25 of the device in the flow-through setting in the setting with a high injection pressure FIG. 28 an axial section as per FIG. 27 of the device in the blocked setting FIG. 29 a depiction as per FIG. 2 of the disclosed device in a fifth embodiment.
Figure 19:
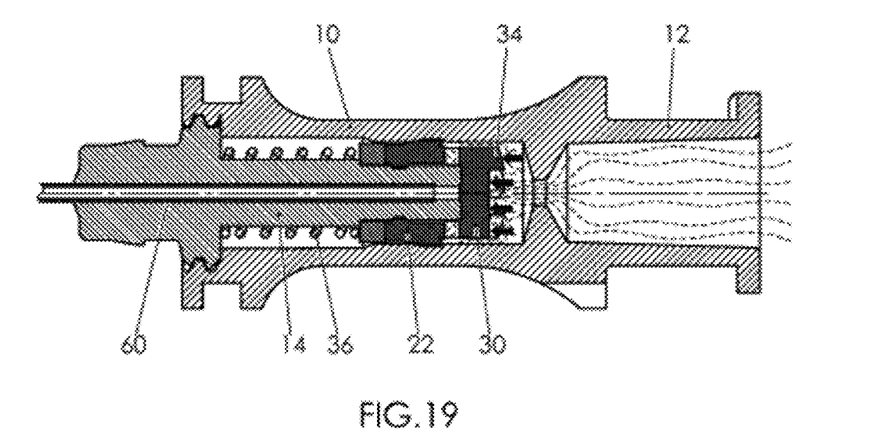

Adjustment sleeve 40 can be lifted axially out of this setting from flange 42, wherein secant surfaces 52 of adjustment sleeve 40 glide on flat surfaces 48 of interior tube 14. When the secant surfaces 52 projecting inward come to cover notches 50.1, adjustment sleeve 40 can be turned about interior tube 14, as is shown in FIGS. 12 and 13, with secant surfaces 52 engaging into notches 50.1, as is evident from FIG. 13. Thereby adjustment sleeve 40 is arrested in the axial position on interior tube 14 corresponding to notches 50.1. Thereby helical compression spring 36 is correspondingly pretensioned, and the spring force acting on plunger 22 is increased, so that the device locks only at the higher injection pressure of 15 psi, for example. If adjustment sleeve 40 is again turned to the angular setting in which secant surfaces 52 align with flat surfaces 48, then secant surfaces 52 get free of notches 50.1 and adjustment sleeve 40 can be lifted in the axial direction further up from flange 42, as is shown in FIG. 14. As soon as secant surfaces 52 come to cover the next pair of notches 50.2, adjustment sleeve 40 again can be turned by 45°, as per the depiction of FIG. 13, so that adjustment sleeve 40 again is arrested in appropriate fashion in notches 50.2. By this means, helical compression spring 36 is pretensioned even more, through which the spring force acting on plunger 22 is further increased. This corresponds to a blocking of the through flow at a correspondingly higher injection pressure of 25 psi, for example.

For adjustment of adjustment sleeve 40, housing 10 has two diametrically situated windows 54 in its jacket surface, through which adjustment sleeve 40 can be grasped with the fingers and slid and twisted. The particular adjustment position of adjustment sleeve 40, and thus the particular set injection pressure, is indicated by a marking 56 on the outer circumference of adjustment sleeve 40 and a scale 58 on windows 54 of housing 10.

FIGS. 15 to 19 show a second embodiment of the disclosed device.

This embodiment is in accord with the first embodiment in the essential function. In this respect the same reference symbols are used, and reference is made to the previous description. The essential difference from the first embodiment is that in this embodiment, the device for limiting injection pressure is integrated into the proximal addition of a cannula, so that it is not a separate component. Since the device for limiting injection pressure is integrated in the cannula addition, thereby the device is assigned to a specific cannula with specifically preset dimensions. Therefore, as a rule, adjustability of the spring force acting on the plunger for adaptation to the injection pressure is dispensed with.

Since in this embodiment no adjustment of the spring force impinging on the plunger is provided, adjustability of the support piece on which helical compression spring 36 is braced, is dispensed with. The support piece is formed by flange 42, with which interior tube 14 is inserted into housing 10. Additionally, a simple integration can be done in such a way that the proximal end of cannula tube 60 of the cannula provided with the device can be inserted coaxially into housing 10 and injected into interior tube 14. By this means the device is substantially simplified and able to be manufactured in an especially cost-effective way, which promotes integration with the disposable cannula.

Figure 20:
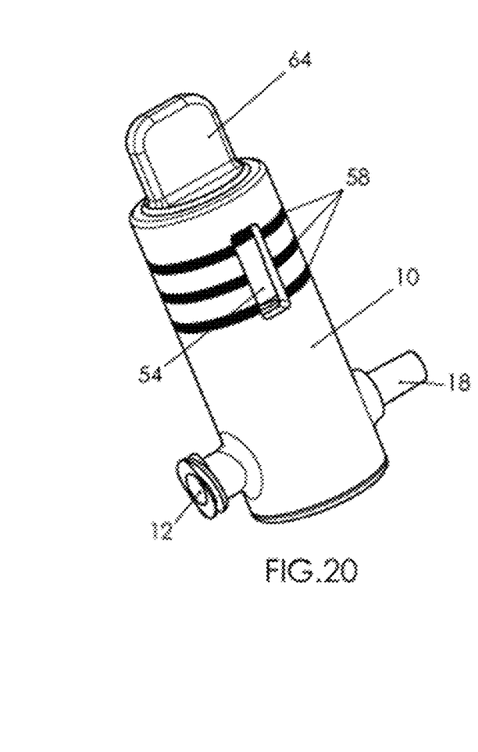
Figure 21:
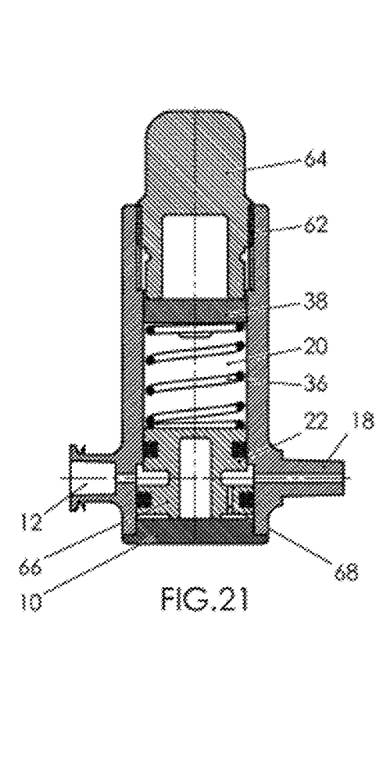
Figure 22:
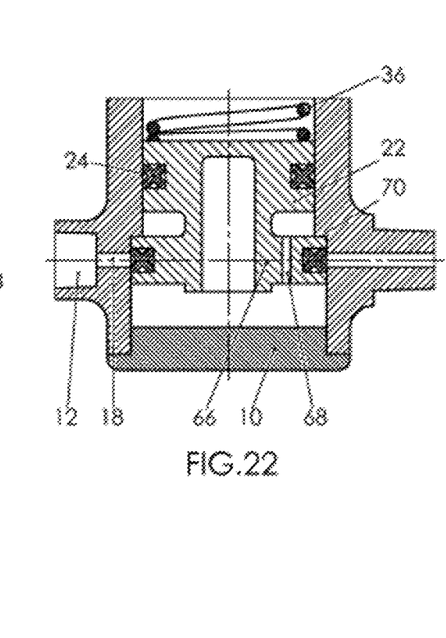
Figure 23:
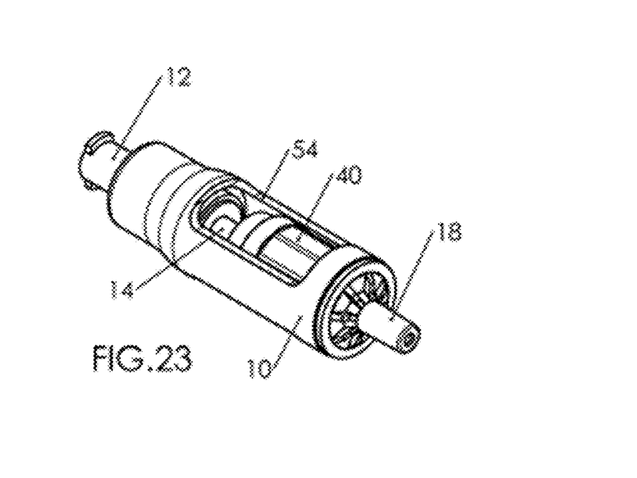
Figure 24:
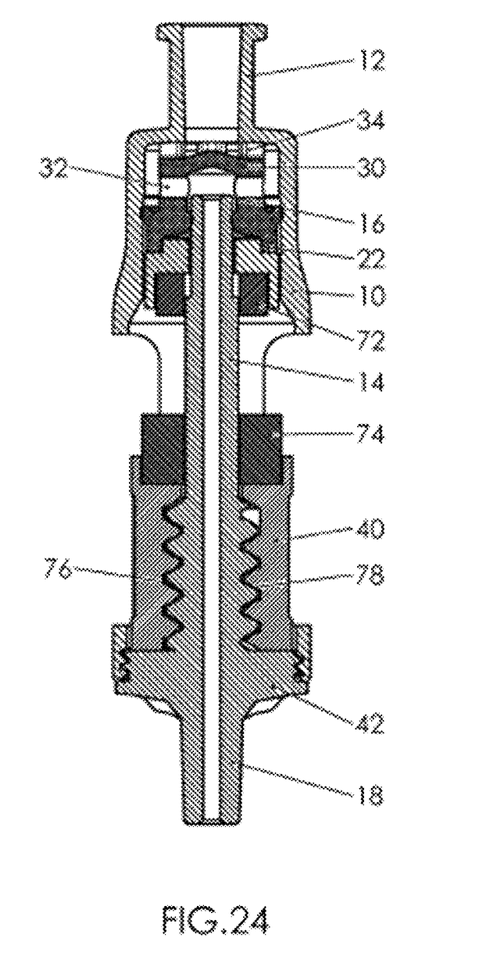
Figure 25:
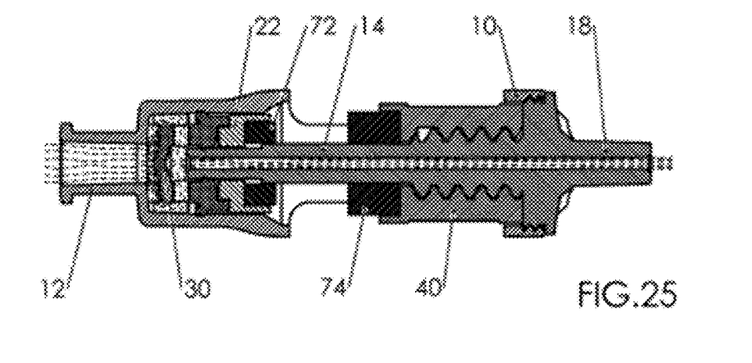
Figure 26:
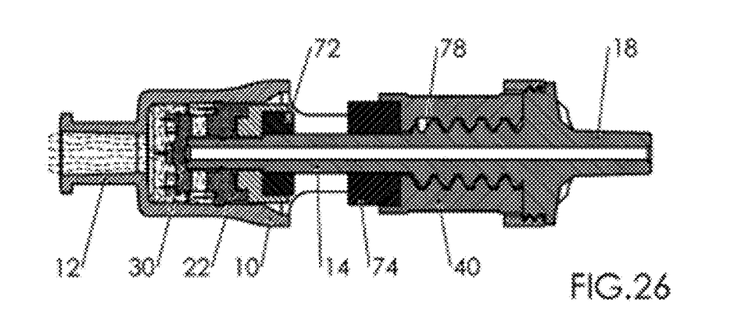

FIGS. 20 to 22 depict a third embodiment of the disclosure.

In this embodiment, housing 10 has an entrance 12 and an outlet 18 aligning with this entrance 12. The entrance 12 and outlet 18 are configured as attachments for connection of a syringe or a cannula. Perpendicular to the longitudinal axis line defined by entrance 12 and outlet 18, housing 10 forms a stroke space 20, in which a plunger 22 is supported, which is movable in the axis of stroke space 20 perpendicular to the longitudinal central axis. Plunger 22 is sealed against the inner wall of housing 10 by means of a sealing lip 24. Housing 10 forms a flow-through channel leading from entrance 12 to outlet 18, which is laterally closed by plunger 22. A spring force acts on plunger 22, which is generated by a helical compression spring 36. Helical compression spring 36 is braced on the one side on plunger 22 and on the other side on a support piece 38. Support piece 38 is inserted into the end of housing 10 that projects out radially and is adjustable axially in the stroke direction of plunger 22 by means of a self-limiting threading 62. For adjustment, a handle 64 projecting out of housing 10 is provided. In the area of the adjustment path of support piece 38, in the wall of housing 10, windows 54 are provided, through which a marking 56 of support piece 38 is visible, and the axial setting of support piece 38 can be read out by means of a scale 58 provided on windows 54. By turning support piece 38, via threading 62, the axial position of support piece 38 and thus the pretensioning of helical compression spring 36 braced on support piece 38 can be adjusted.

On the front surface of plunger 22 that faces the flow-through channel, a valve shifter 66 serving as a blocking element is attached. The valve shifter has the function of releasing entrance 12 into the housing depending on the setting of valve shifter 66, to make possible through-flow to outlet 18, or to close inlet 12, to close off the through-flow. In the embodiment depicted, valve shifter 66 has the form of a circular disk, which is at an axial distance from the front surface of plunger 22, corresponding in outer diameter to the inner diameter of stroke space 20 and having an axial thickness that is greater than the inner diameter of entrance 12. Valve shifter 66 can be moved by means of plunger 22 between a flow-through setting shown in FIG. 21 and a blocked setting shown in FIG. 22. In the flow-through setting, valve shifter 66 is below the flow-through channel leading from entrance 12 to outlet 18, so that the fluid introduced through entrance 12 can flow between valve shifter 66 and plunger 22 to outlet 18. In the blocked setting (FIG. 22), valve shifter 66 is raised by means of plunger 22, so that it closes entrance 12, through which the flow through from entrance 12 to outlet 18 is blocked.

The manner of functioning of the device in this third embodiment matches the functioning that is described in connection with the first embodiment, so that reference is made thereto.

As long as the injection pressure that forms in the cannula and the flow-through channel is less than the pressure acting by spring force on plunger 22, helical compression spring 36 holds the plunger in the lower setting depicted in FIG. 21, in which valve shifter 66 allows passage from entrance 12 to outlet 18 and thus from the syringe to the cannula. If the injection pressure rises above the value set by pretensioning of helical compression spring 36, then this injection pressure builds up in the flow-through channel between plunger 22 and valve shifter 66. This stagnation pressure also acts via passage openings 68 in the space beneath valve slider 66. This stagnation pressure in excess of the preset value presses plunger 22 and valve shifter 66 upward against the force of helical compression spring 36 (in the depiction of FIGS. 21 and 22), so that valve slider 22 gets into the locked setting shown in FIG. 22, in which it closes entrance 12 and thus closes off inflow of anesthetic to the cannula. In this locked setting, valve shifter 66 comes to rest at a stop 70, so that it no longer can be compressed out by stagnation pressure beyond the locked setting.

FIGS. 23 to 28 show a fourth embodiment of the device. The device in this embodiment essentially corresponds to the embodiment in FIGS. 1 to 8. If correspondences of FIGS. 1 to 8 exist to this embodiment, the same reference numbers are therefore used, and reference is made to the previous description.

The embodiment of FIGS. 23 to 28 differs in essence from the embodiment of FIGS. 1 to 8 in that the resetting force acting on plunger 22 is not generated as a spring force of a helical compression spring for example, but by a magnetic force. Such a magnetic resetting force is described in FIGS. 23 to 28 in an embodiment that corresponds to the embodiment of FIGS. 1 to 8. It is readily seen that a magnetic resetting force instead of the resetting force of a helical compression spring is also possible in the embodiment of FIGS. 15 to 19 and in the embodiment of FIGS. 20 to 22.

In the fourth embodiment, interior tube 14, valve seat 16, plunger 22, stub 28, valve disk 30, flow-through openings 32 and spacer tabs 34 correspond to the first embodiment form, as they are described in particular in connection with this first embodiment form.

Two magnets 72 and 74 generate the resetting force acting on plunger 22, which in particular are configured as permanent magnets. The one magnet 72 is attached on the front surface of plunger 22 directed downstream. The other magnet 74 is attached on the first surface of support piece 38 directed upstream. Magnets 72 and 74 have pole arrangements so that they mutually repel. Magnet 72, together with plunger 22, is guided so as to slide axially on interior tube 14. The other magnet 74 can be attached in fixed fashion on a support piece formed by an inside collar of housing 10. In this case, the magnetic force acting on plunger 22 has a preset fixed value, which limits injection pressure.

Figure 27:
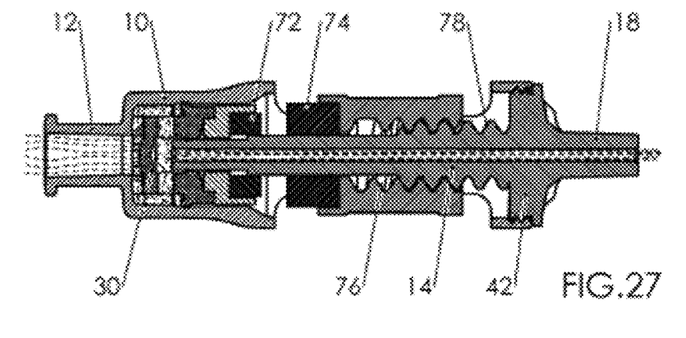
Figure 28:
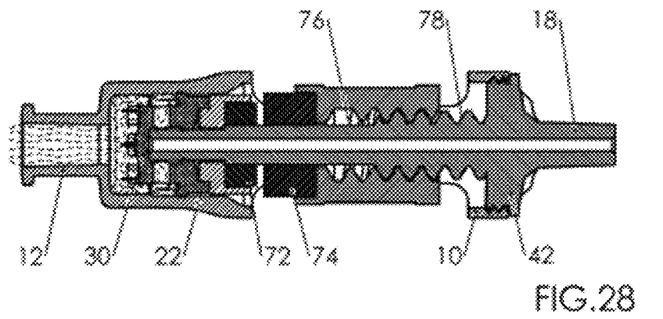

If the resetting force, and thus the value limiting the injection pressure is to be adjustable, then support piece 38 is axially adjustable in the housing, as this is depicted in the embodiment of FIGS. 23 to 28. Support piece 38, on which magnet 74 is attached, in this embodiment is configured as adjustment sleeve 40, which engages with an interior threading 76 into an exterior threading 78 of interior tube 14. In the setting shown in FIGS. 25 and 26, with low injection pressure, adjustment sleeve 40 is turned on interior tube 14 downstream, i.e, to the right in the drawing, until adjustment sleeve 40 comes to rest on flange 42, by which interior tube 14 is screwed into housing 10. Magnets 72 and 74 in this setting have the maximum interval to each other, so that the magnetic force acting on plunger 22 is small. If adjustment sleeve 40 is turned upstream by means of the threading 76, 78 on interior tube 14, then the axial interval between magnet 72 attached to plunger 22 and magnet 74 attached to adjustment sleeve 40 is reduced, so that the magnetic repelling power between magnets 72 and 74, and thus the resetting force acting on plunger 22, increases. This setting is shown in FIGS. 27 and 28. In correspondence to the higher resetting force, the device locks at a higher pressure of the fluid in the flow-through channel.

Figure 29:
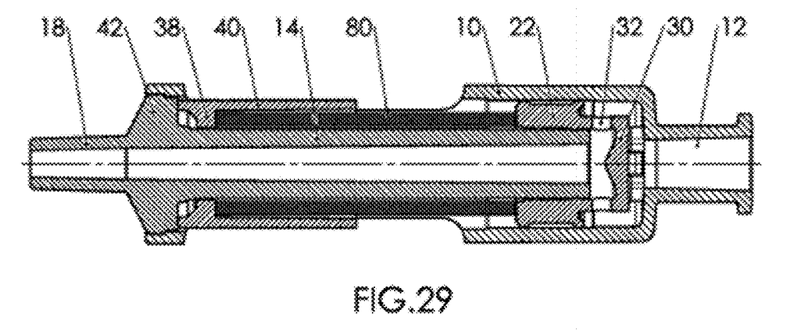

FIG. 29 shows another altered embodiment form, which in essence corresponds to the first embodiment. Therefore, the same reference numbers are used, and reference is made to the detailed description of the first embodiment. The fifth embodiment differs from the first embodiment in that, instead of helical compression spring 36 for generation of a resetting force on plunger 22, an elastically compressible element 80 is used, which coaxially surrounds interior tube 14 and is braced on the one side on plunger 22 and on the other side on support piece 38. Elastically compressible element 80 can for example consist of a rubber-elastic material or an elastically compressible foam. It is also possible to use a closed air or gas volume as the compressible element 80. All that is essential is that the elastically compressible element 80 generates a resetting force dependent on the axial compression. Naturally such an elastically compressible element 80 can also be used with the embodiment forms of FIGS. 15-19 and 20-22 instead of helical compression spring 36.

LIST OF REFERENCE SYMBOLS

| | |
|---|---|
| 10 | housing |
| 12 | entrance |
| 14 | Interior tube |
| 16 | Valve seat |
| 18 | outlet |
| 20 | Stroke space |
| 22 | plunger |
| 24 | Outer sealing lip |
| 26 | Inner sealing lip |
| 28 | stub |
| 30 | Valve disk |
| 32 | Flow-through opening |
| 34 | Spacer tabs |
| 36 | Helical compression spring |
| 38 | Support piece |
| 40 | Adjustment sleeve |
| 42 | flange |
| 44 | nose |
| 46 | recess |
| 48 | Flat surfaces |
| 50 | notches |
| 52 | Secant surfaces |
| 54 | window |
| 56 | marking |
| 58 | scale |
| 60 | Cannula tube |
| 62 | threading |
| 64 | handle |
| 66 | Valve shifter |
| 68 | Passage opening |
| 72 | magnet |
| 74 | magnet |
| 76 | Interior threading |
| 78 | Exterior threading |
| 80 | Compressible element |

The invention claimed is:

1. A device for limitation of the injection pressure of a medical instrument for introduction of a fluid, comprising:
   a housing, the housing comprising:
      an entrance for introducing the fluid at an entry pressure;
      an outlet for introducing the fluid to the instrument;
      a flow-through channel connecting the entrance and the outlet;
   a plunger guided in the housing and which is impinged on by pressure of the fluid and through the pressure is movable against a resetting force;
   a blocking element arranged on the plunger and located in a flow cross section of the flow-through channel,
   wherein the blocking element releases the flow cross section, when the pressure of the fluid impinging on the plunger is less than a value preset by the resetting force, and blocks the flow cross section when the pressure of the fluid impinging on the plunger exceeds the value preset by the resetting force and moves the plunger against the resetting force.

2. The device of claim 1, characterized in that wherein the resetting force is adjustable.

3. The device of claim 2,
   wherein for adjustment of the resetting force, the support piece is axially adjustable in the housing.

4. The device of claim 1, wherein the housing further comprises a stroke space, in which the plunger is axially guided in sealed fashion, and that the resetting force acts coaxially to a plunger motion direction and engages on one side on the plunger and on another side on a support piece of the housing.

5. The device of claim 4,
   wherein the entrance and the outlet are arranged on a common longitudinal axis line and that the stroke space is configured in the housing to be coaxial to a longitudinal axis line of the housing.

6. The device of claim 5,
   wherein the outlet is configured as an interior tube projecting coaxially into the housing, which empties into the stroke space with one open end lying upstream, that the plunger is guided on the interior tube and that the blocking element is a valve disk that is axially attached to the plunger, which sits the valve disk sitting in sealing fashion axially on an open end of the interior tube, to block the flow cross section, and which is axially displaced from the open end of the interior tube to release the flow cross section.

7. The device of claim 4,
   wherein the entrance and the outlet are arranged in a longitudinal axis line and that the stroke space is configured in the housing with an axis perpendicular to the longitudinal axis line.

8. The device of claim 7,
   wherein the blocking element is a valve shifter attached on a side of the plunger facing the flow-through channel, which is moved on the longitudinal axis line and closes the entrance to block the flow cross section and is moved out perpendicular from the longitudinal axis line to release the flow cross section.

9. The device of claim 1,
   wherein the resetting force is affected by a helical compression spring coaxial to a direction of plunger motion, wherein the spring is braced on the one side on the plunger and on the other side on the support piece of the housing.

10. The device of claim 1,
    wherein the resetting force is affected by an elastically compressible element in the direction of plunger motion, which is braced on the one side on the plunger and on the other side on the support piece of the housing.

11. The device of claim 1,
    wherein the resetting force is affected by repelling permanent magnets, of which one is arranged on the plunger and the other on a support piece of the housing.

12. The device of claim 1,
    wherein the device is a separate component, which is able to be connected with an attachment forming the entrance and with an attachment forming the outlet.

13. The device of claim 1,
    wherein the device is integrated in a proximal attachment of a cannula.

14. A device for limiting fluid injection pressure of a medical instrument, comprising:
    a housing with a fluid entrance, a fluid outlet, a channel connecting the fluid entrance and fluid outlet, a flow cross section, a stroke space and a resetting force support piece, wherein the fluid entrance and the fluid outlet are arranged along a longitudinal axis of the housing and the stroke space is configured in the housing with an axis perpendicular to the longitudinal axis of the housing;
    a plunger biased in the housing in an open position with an adjustable resetting force, the plunger being movable from pressure of a fluid against the resetting force to a closed position;
    a blocking element arranged on the plunger and located in the flow cross section of the channel,
    wherein the blocking element blocks the flow cross section when the pressure of the fluid against the plunger exceeds the resetting force and moves the plunger against the resetting force, and
    wherein the blocking element unblocks the flow cross section, when the pressure of the fluid against on the plunger is less than the resetting force.

15. The device according to claim 14, wherein the support piece is axially adjustable in the housing for adjusting the resetting force.

16. The device according to claim 14, further comprising:
    a helical compression spring coaxial to a direction of plunger motion that provides the resetting force, wherein the spring is braced between the plunger and the resetting force support piece of the housing.

17. The device according to claim 14, further comprising:
    an elastically compressible element in a direction of plunger motion that provides the resetting force, wherein the elastically compressible element is braced between the plunger and the resetting force support piece of the housing.

18. The device according to claim 14, further comprising:
    repelling magnets that provide the resetting force, wherein one magnet of the magnets is arranged on the plunger and the other magnet is arranged on the resetting force support piece of the housing.

19. The device according to claim 14,
    wherein the blocking element is a valve shifter attached on a side of the plunger facing the channel,
    wherein the valve shifter is moved on the longitudinal axis of the housing to closes the fluid entrance to block the flow cross section and is moved out perpendicular from the longitudinal axis of the housing to unblock the flow cross section.

20. The device according to claim 14, wherein the housing is a proximal attachment of a cannula.

\* \* \* \* \*